(12) United States Patent
Steenkeste et al.

(10) Patent No.: US 7,959,585 B2
(45) Date of Patent: Jun. 14, 2011

(54) DEVICE AND METHOD FOR THE TIME-BASED ANALYSIS OF THE AGITATION OF A BEDRIDDEN PATIENT

(75) Inventors: Francois Steenkeste, Laurac le Grand (FR); Pierre Rumeau, Portet sur Garonne (FR)

(73) Assignee: INSERM (Institut National de la Santé et de la Recherche Médicale), Paris (FR)

( * ) Notice: Subject to any disclaimer, the term of this patent is extended or adjusted under 35 U.S.C. 154(b) by 102 days.

(21) Appl. No.: 12/440,800

(22) PCT Filed: Sep. 11, 2007

(86) PCT No.: PCT/FR2007/051909
§ 371 (c)(1),
(2), (4) Date: Mar. 11, 2009

(87) PCT Pub. No.: WO2008/031984
PCT Pub. Date: Mar. 20, 2008

(65) Prior Publication Data
US 2009/0281461 A1 Nov. 12, 2009

(30) Foreign Application Priority Data
Sep. 13, 2006 (FR) ..................... 06 08014

(51) Int. Cl.
*A61B 5/103* (2006.01)
*A61B 5/117* (2006.01)

(52) U.S. Cl. ....................... 600/595; 600/587

(58) Field of Classification Search ................. 600/300, 600/301, 304, 587–595; 702/1, 127, 138–154
See application file for complete search history.

(56) References Cited

U.S. PATENT DOCUMENTS

| | | | | |
|---|---|---|---|---|
| 5,515,865 A | * | 5/1996 | Scanlon | 600/534 |
| 5,590,650 A | * | 1/1997 | Genova | 600/301 |
| 5,668,780 A | | 9/1997 | Hsieh | |
| 5,853,005 A | * | 12/1998 | Scanlon | 600/459 |
| 6,280,392 B1 | * | 8/2001 | Yoshimi et al. | 600/534 |
| 6,984,207 B1 | * | 1/2006 | Sullivan et al. | 600/301 |

FOREIGN PATENT DOCUMENTS
EP 1 435 606 A 7/2004

OTHER PUBLICATIONS

Schaff et al: "Aide technique a l'evaluation des patients crieurs alites" ITBM-RBM, Editions Scientifiques Et Medicales Elsevier, Oct. 2005, pp. 357-362, vol. 26, No. 5-6, XP005196116.
French Search Report in Corresponding Application No. FA 684621/FR 0608014 dated May 15, 2007.
International Search Report in Corresponding Application No. PCT/FR2007/051909 dated Mar. 6, 2008.

\* cited by examiner

*Primary Examiner* — Jeffrey G Hoekstra
(74) *Attorney, Agent, or Firm* — Young & Thompson

(57) ABSTRACT

Device for the time-based analysis of the agitation of a bedridden patient includes elements (4) for acquiring the patient's shouts and elements (5) for acquiring the patient's movements, the acquisition elements being connected to storage elements (9) suitable for storing the acquired data accompanied by a time stamping of the latter, the storage elements being connected to analysis and presentation elements (10) suitable for providing care staff with a representation of the frequency and duration of the patient's shouts and movements which are representative of the patient's agitation over a determined time span, characterized in that the elements for acquiring shouts include a bandpass filter (6) suitable for isolating the shouts from speech and ambient noise.

3 Claims, 3 Drawing Sheets

Figure 1:
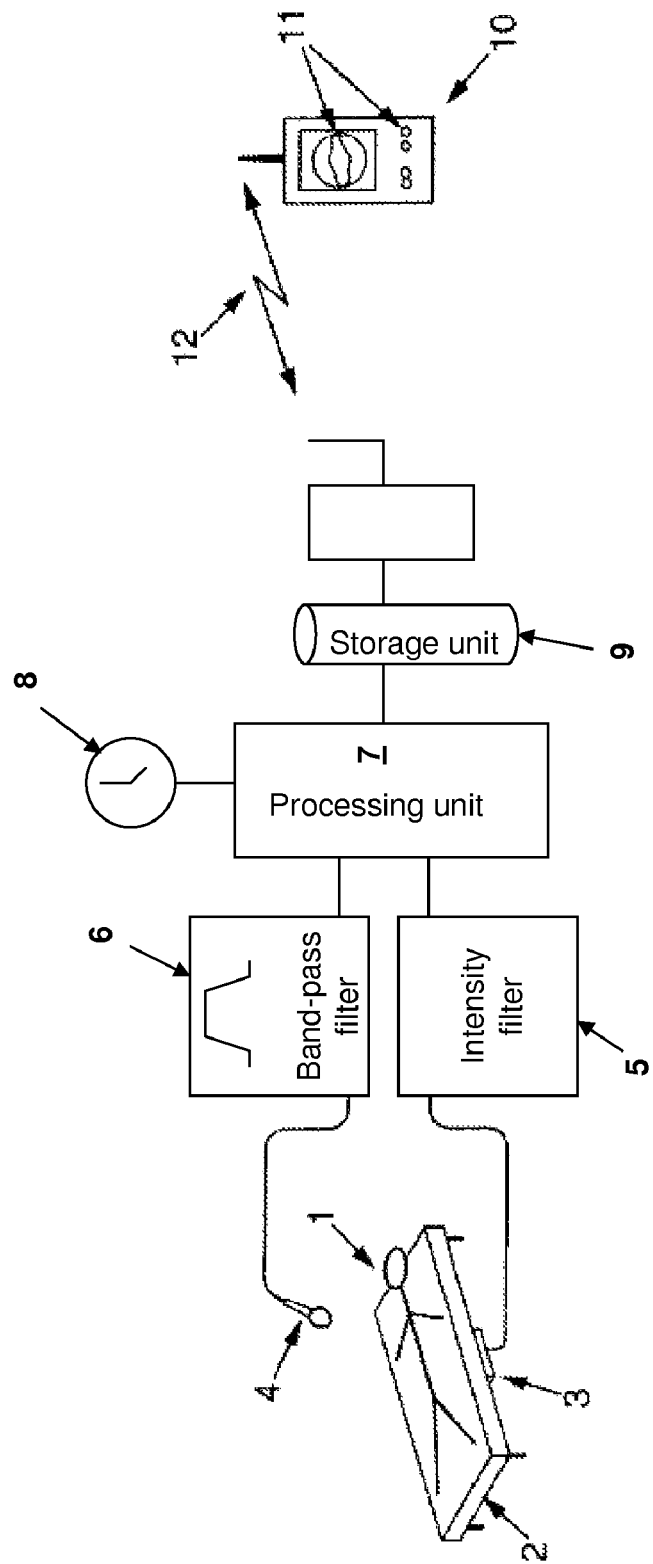

DEVICE AND METHOD FOR THE TIME-BASED ANALYSIS OF THE AGITATION OF A BEDRIDDEN PATIENT

The present invention relates to a device and a method for the time-based analysis of the agitation of a bedridden patient.

Hospital psychiatry and gerontology departments often have to look after patients known as "shouters".

These are patients who, for reasons which are often difficult to determine, suddenly become agitated in bed and start shouting for an indeterminate period.

The population of these "shouter" patients is increasing steadily with the increase in life expectancy and the prevalence of age-related diseases such as Alzheimer's disease.

These patients represent a very heavy burden for care staff, as their shouts disturb the everyday life of the departments in which they are to be found.

The study of these shouts is currently very difficult to the extent that, in order to try and find the cause of these shouts, it is first necessary to be able to quantify them in terms of duration, intensity and time. Until recently, this quantification was based only on handwritten notes made by the care staff with the lack of reliability of measurements associated with such a method.

The document "Aide technique à l'évaluation des patients crieurs alités" [*Technical aid for the evaluation of bedridden shouter patients*], M. Schaff et al., ITMB. RBM 26(2005) 357-362 describes a measurement system based on an infrared sensor for detecting the agitation of the patients and a microphone for detecting shouts the volume of which exceeds a preset sound threshold.

This data picked up in this way is processed in order to be able to display the results in the form of a diagram which is representative of the day. The medical staff can thus seek the most suitable treatment in order to minimize the patient's shouts and agitation.

Now, the system described has the drawback of being very sensitive to the patient's environment such as voices and noises generated by people present in the room. This drawback makes the system unsuitable for use in a hospital or nursing home environment in which it is impossible to guarantee silence.

The detection of the patient's movements by the infrared camera has the drawback of requiring relatively significant computing power for image processing making it possible to distinguish between a simple natural movement, for example the patient turning over in bed, and the agitation manifested by sudden movements.

It is therefore desirable to have available a device for measuring the agitation of a patient, which is sufficiently selective to isolate the shouts and agitation of the bedridden patient from the noises generated by the environment.

It is also desirable for the device to have a relatively low cost in order to be able to equip a number of beds. In fact, the abovementioned document shows that it is often necessary to record the patient's agitation over long periods before determining the most suitable treatment.

It is also desirable to have a device which is capable of distinguishing a simple movement from sudden agitation in simple and inexpensive manner.

In order best to tackle one or more of these concerns, in a first aspect of the invention, a device for the temporal analysis of the agitation of a bedridden patient is presented. This device comprises means for acquiring the patient's shouts and means for acquiring the patient's movements. These acquisition means are connected to storage means suitable for storing the acquired data accompanied by time-stamping of the latter. The storage means are connected to analysis and presentation means suitable for providing the care staff with a representation of the frequency and duration of the patient's shouts and movements which are representative of the patient's agitation over a determined time span. The means for acquiring shouts comprise a band-pass filter suitable for isolating shouts from speech and ambient noise.

In a second aspect of the invention, a method for the temporal analysis of the agitation of a bedridden patient comprises the steps of:
a. acquisition of the patient's shouts, and
b. acquisition of the patient's movements,
c. storage of the data acquired accompanied by time-stamping of the latter,
d. analysis and presentation of the time-stamped data suitable for providing care staff with a representation of the frequency and duration of the patient's shouts and movements which are representative of the patient's agitation over a determined time span,
   characterized in that the acquisition of the shouts comprises a band-pass filtering sub-step suitable for isolating shouts from speech and ambient noise.

Other characteristics of particular embodiments are described in the dependent claims.

Thus, the frequency filtering of the sounds advantageously makes it possible to easily distinguish the patient's shouts from the surrounding noise.

Similarly, the use of a vibration sensor advantageously simplifies the detection of sudden movements and makes it possible to only use low-power computing means, such as an 8-bit microcontroller.

It is understood that it is thus possible to implement the invention using common, low-cost equipment thus making it possible to manufacture devices at low cost.

Figure 2:
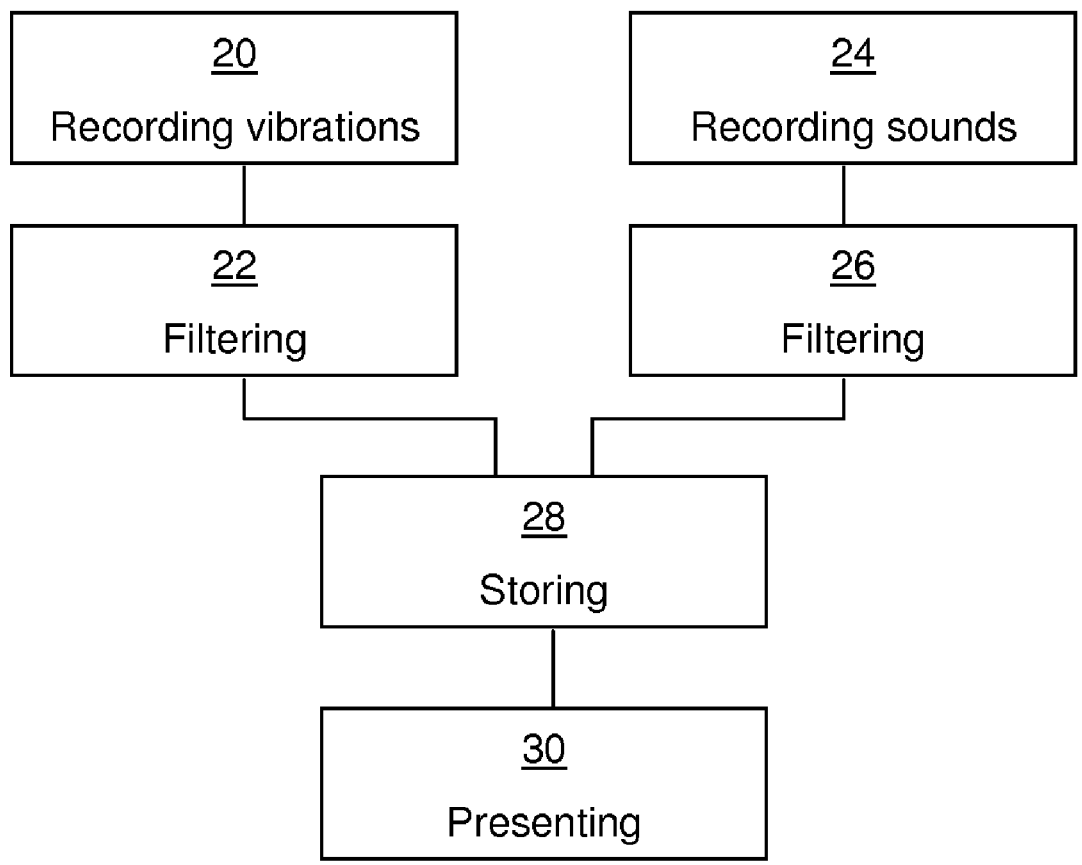
Figure 3:
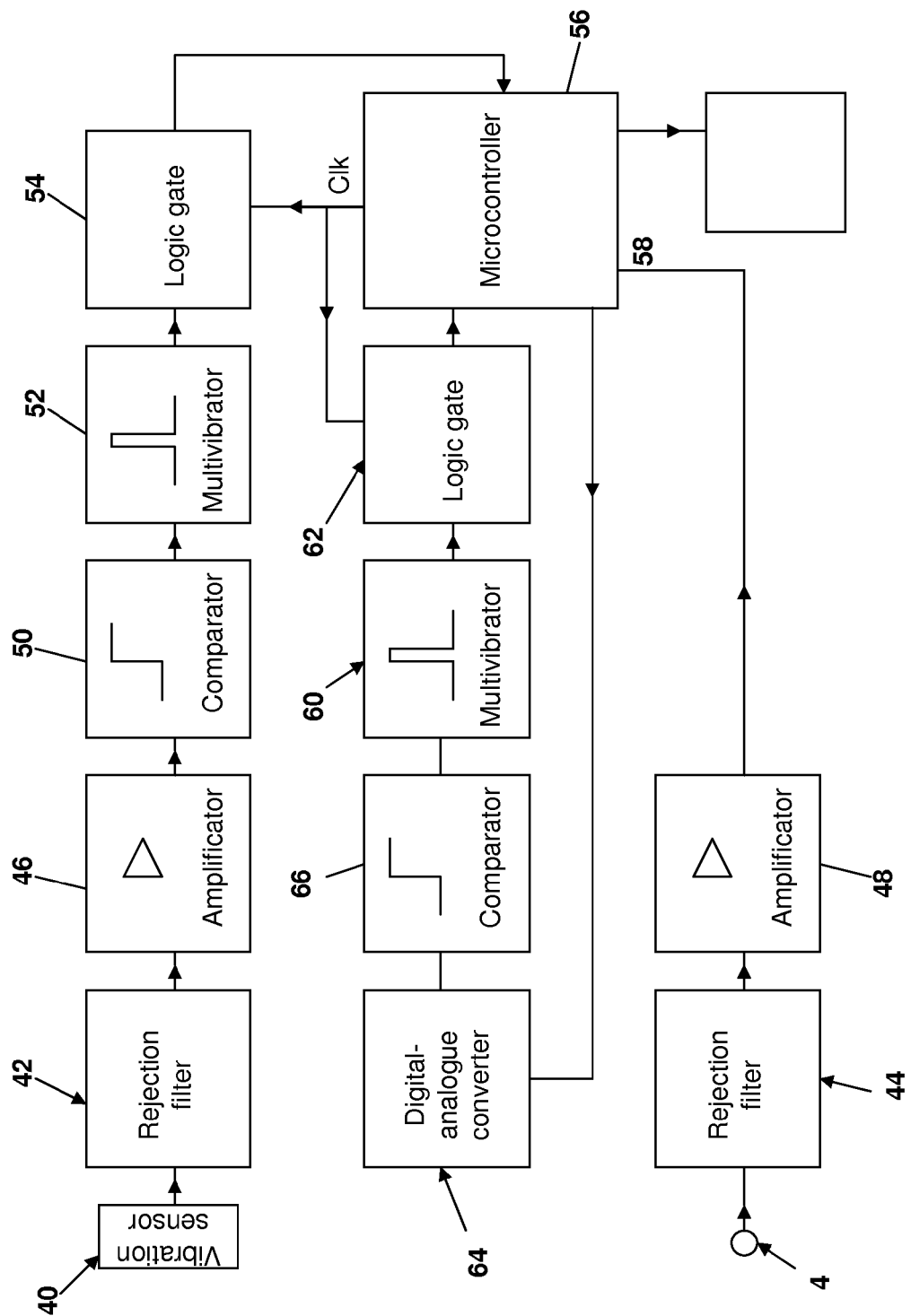

The invention will be better understood on reading the following description, given solely by way of example and with reference to the attached figures, in which:

FIG. 1 is a diagrammatic view of a device according to an embodiment of the invention; and, FIG. 2 is a flowchart of the operation of the device of FIG. 1; and FIG. 3 is a diagrammatic view of the measuring circuit in a particular embodiment.

With reference to FIG. 1, a patient 1 is confined to a bed 2 fitted with a device 3 for acquiring the patient's movements.

This device 3 for acquiring movements is preferably a sensor connected to the bed frame in order to be able to pick up the vibrations of the bed produced by the movements of the patient 1.

A microphone 4 is installed preferably above the bed in order to pick up the noises, and in particular the shouts, originating from the patient 1.

The device 3 for acquiring movements is connected to an intensity filter 5. This filter 5 is adjustable so that only information corresponding to vibrations greater than a predetermined minimum intensity is transmitted.

The microphone 4 is connected to a band-pass filter 6 suitable for isolating a patient's shouts from the surrounding noise, such as the voices of the care staff.

The filters 5, 6 are connected to a processing unit 7 comprising a clock 8 allowing the time-stamping of the information acquired.

A storage unit 9 allows storage of the information.

For consultation, a terminal 10 comprising a human-machine interface 11 is connected to the storage unit 9 by a wired or wireless data link 12.

The operation of the device for analysis of the agitation is the following, FIG. 2.

The vibrations of the bed caused by the patient's sudden movements are recorded in 20 by the vibration sensor 3.

The signal generated by the sensor 3 is filtered in step 22 by the intensity filter 5 in order to retain only the signals corresponding to sudden gestures of a certain amplitude and not simple movements.

In parallel, the microphone 4 records in step 24 the sounds originating from the bed 2. The corresponding electrical signal generated by the microphone 4 is filtered in step 26 by the band-pass filter 6 in order to separate shouts from ambient noises such as the voices of the care staff. The band-pass filter is parameterizable in order to be adjusted to the frequency ranges of the patient's shouts. In fact it is understood that the shouts of a woman are in a more acute frequency range than the shouts originating from a man.

Similarly, the band-pass filter 6 is advantageously completed by intensity filtering allowing only sounds greater than a minimum power to pass.

The signals generated by the shouts, like those generated by sudden movements of the patient are stored in step 28 in a database accompanied by the date and time of their recording.

When a doctor wishes to study the patient's behaviour, he uses a terminal 10 which can be a simple personal computer or a palmtop computer.

On interrogation by the doctor, the terminal recovers in step 30 the data stored and presents them to the doctor for example in the form of a graph of episodes of shouts/agitation as a function of time.

In a particular embodiment, FIG. 3, the device 3 for acquiring movement comprises a piezo-electric vibration sensor 40.

The signals originating from the microphone and the piezoelectric sensor are filtered by a 50 Hz rejection filter 42, 44 then amplified in 46, 48.

After amplification, the signals from the vibration sensor are compared with an adjustable voltage in a comparator 50 the output of which is a digital signal sent to a retriggerable monostable multivibrator 52 in order to obtain a pulse with a minimum calibrated width of 0.5 sec. This pulse triggers a logic gate 54 receiving at its other input a clock signal Clk of 4,096 Hz originating from a microcontroller 56. This results in a sequence of pulses of greater or lesser duration, the number of pulses depending on the duration of the agitation.

This sequence of pulses arrives at the input of a counter of the microcontroller. At regular intervals, for example every hour, the microcontroller stores the content of this counter in a different memory location.

The amplified signals from the microphone are directed to the input 58 of an analogue-to-digital converter of the microcontroller 56. The sequence of the digital values obtained is then processed in a digital band-pass filter in order to isolate the frequencies contained in the shouts and to reject the frequencies contained in speech. A software parameterization makes it possible to select a woman's shouts or a man's shouts.

The band-pass filter advantageously uses the Z-transform technique which makes it possible to obtain a recurrence function all the coefficients of which are integers. Thus, it is possible to use an 8-bit microcontroller, which is therefore low-cost, in order to perform the calculations in a short time, typically of the order of 100 μs. The audio signal is thus sampled at the maximum frequency of 10 kHz which allows good spectral analysis of the sound signal.

A switch makes it possible to choose between the two sampling frequencies of 6 kHz or 10 kHz.

In the first case, the pass-band of the filter, linked to the transfer function utilized, has a width of approximately 1500 Hz and is centred on approximately 2500 Hz. In the second case, the pass-band has a width of approximately 900 Hz and is centred on approximately 1500 Hz.

The first pass-band is more particularly suitable for women's voices whereas the second is more suitable for men's voices.

At the output from the digital band-pass filter, and if a shout is detected, the microcontroller sends a pulse to the input of a retriggerable monostable multivibrator 60 which controls a logic gate 62. This pulse is generated by sending a digital signal corresponding to the filtered shout to an digital-analogue converter 64 the output of which is connected to a comparator 66. As for the vibrations, this makes it possible to retain only the shouts having a certain intensity.

Depending on the command, this logic gate 62 allows a clock pulse sequence of greater or lesser duration to pass, the length of the sequence being proportional to the duration of the shouts.

The sequence of pulses is directed to the input of a second counter of the microcontroller. In the same manner as for the agitations, the microcontroller counts the pulses which reach this counter at regular intervals, for example hour by hour, and stores the total in particular memory locations.

When the medical staff wish to obtain the counts of the patient's shouts and agitations, they interrogate the device using a mobile graphic display and calculation unit (palmtop computer, laptop, tablet pc or smart phone equipped with Bluetooth technology). An application installed in the mobile unit makes it possible to link to the device via a Bluetooth radio-type connection. The data being downloaded to the mobile device, the results are displayed on the screen in the form of a double histogram.

The invention claimed is:

1. A device for a time-based analysis of the agitation of a bedridden patient comprising:
   means (4) for acquiring data related to the patient's shouts; and
   means (3) for acquiring data related to the patient's movements, the acquisition means being connected to storage means (9) suitable for storing the acquired data accompanied by time-stamping (8) of said acquired data, connected to analysis and presentation means (10, 11) suitable for providing care staff with a representation of frequency and duration of the patient's shouts and movements which are representative of the patient's agitation over a determined time span,
   wherein the means (4) for acquiring data related to the shouts comprise a band-pass filter (6) suitable for isolating shouts from speech and ambient noise, the band-pass filter comprising pass-band selection means between two predetermined bandwidths, said two predetermined bandwidths having a bandwidth of approximately 1500 Hz centered on 2500 Hz for the first and a bandwidth of approximately 900 Hz centered on 1500 Hz for the second, and
   the means for acquiring data related to the movements comprise a sensor of the vibrations of a patient's bed and an intensity filter adapted so that only the vibrations having an intensity above a predetermined threshold are stored in the storage means.

2. The analysis device according to claim 1, wherein the band-pass filter is a digital filter based on a Z-transform technique.

3. A method for a time-based analysis of the agitation of a bedridden patient comprising the steps of:

acquisition (24, 26) of data related to the patient's shouts;
acquisition (20, 22) of data related to the patient's movements,
storage (28) of the data acquired accompanied by time-stamping of said acquired data; and
analysis and presentation (30) of the time-stamped data for providing care staff with a representation of frequency and duration of the patient's shouts and movements which are representative of the patient's agitation over a determined time period,
wherein the acquisition of data related to the shouts comprises a band-pass filtering substep suitable for isolating shouts from speech and ambient noise, the band-pass filtering comprising a preliminary step of pass-band selection between two predetermined bandwidths, said two predetermined bandwidths having a bandwidth of approximately 1500 Hz centered on 2500 Hz for the first and a bandwidth of approximately 900 Hz centered on 1500 Hz for the second, and
wherein the step of acquisition of data related to the movements comprises a sub-step of acquisition of vibrations of a patient's bed, followed by an intensity filtering sub-step adapted such that only the vibrations having an intensity above a predetermined threshold are stored.

* * * * *